United States Patent [19]

Holmwood et al.

[11] Patent Number: 4,840,961
[45] Date of Patent: Jun. 20, 1989

[54] HETEROCYCLIC AMIDE DERIVATIVES

[75] Inventors: Graham Holmwood, Wuppertal; Joachim Weissmüller, Monheim; Wilhelm Brandes, Leichlingen; Paul Reinecke, Leverkusen, all of Fed. Rep. of Germany

[73] Assignee: Bayer Aktiengesellschaft, Leverkusen, Fed. Rep. of Germany

[21] Appl. No.: 851,057

[22] Filed: Apr. 11, 1986

[30] Foreign Application Priority Data

Apr. 13, 1985 [DE] Fed. Rep. of Germany ........ 3513259

[51] Int. Cl.$^4$ .................. C07D 233/90; A61K 31/415
[52] U.S. Cl. ..................................... 514/399; 514/255; 514/256; 514/354; 514/355; 514/383; 514/400; 544/335; 544/406; 546/323; 548/262; 548/341; 548/343
[58] Field of Search ............... 514/255, 256, 354, 383, 514/399, 400; 544/335, 406; 546/323; 548/262, 341, 343

[56] References Cited

U.S. PATENT DOCUMENTS

| | | | |
|---|---|---|---|
| 3,308,131 | 3/1967 | McKusick | 548/262 |
| 3,991,071 | 11/1976 | Brookes et al. | 548/341 |
| 4,438,125 | 3/1984 | Hubele et al. | 514/383 |
| 4,442,117 | 4/1984 | Kunz et al. | 514/383 |
| 4,505,922 | 3/1985 | Jager et al. | 514/383 |
| 4,587,239 | 5/1986 | Regel et al. | 514/383 |

FOREIGN PATENT DOCUMENTS

| | | | |
|---|---|---|---|
| 0024017 | 2/1981 | European Pat. Off. | 544/335 |
| 0076030 | 4/1983 | European Pat. Off. | 548/262 |
| 3339644 | 5/1984 | European Pat. Off. | 546/323 |
| 0121344 | 10/1984 | European Pat. Off. | 548/262 |
| 3102590 | 8/1982 | Fed. Rep. of Germany | 548/262 |

*Primary Examiner*—Mary C. Lee
*Assistant Examiner*—E. Brenden Magrab
*Attorney, Agent, or Firm*—Sprung Horn Kramer & Woods

[57] ABSTRACT

Novel heterocyclic amide derivatives of the formula

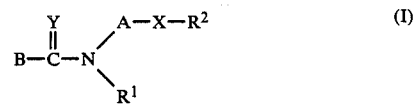

in which

R$^1$ represents alkyl, or represents alkenyl which has more than 2 carbon atoms and is optionally substituted by halogen, or represents alkinyl which has more than 2 carbon atoms and is optionally substituted by halogen, or represents alkoxyalkyl or alkylthioalkyl;

R$^2$ represents optionally substituted naphthyl, or represents optionally substituted tetrahydronaphthyl, or represents optionally substituted indanyl;

A represents an alkylene bridge, or also an alkenylene bridge if X denotes a direct bond;

X represents oxygen, sulphur or a direct bond;

Y represents oxygen or sulphur;

B represents imidazol-1-yl, pyridin-3-yl, pyrazin-2-yl, pyrimidin-5-yl, 1,2,4-triazol-1-yl or 1-methyl-imidazol-5-yl-;

and their acid addition salts and metal salt complexes, are outstandingly active as fungicides.

12 Claims, No Drawings

HETEROCYCLIC AMIDE DERIVATIVES

The present invention relates to new heterocyclic amide derivatives, to fungicidal compositions containing them, and to their use as fungicides.

It has been disclosed that certain amide derivatives, such as, for example, N-[2-(2,4,6-trichlorophenoxy)ethyl]-N-propyl-1H-imidazole-1-carboxamide (compare DE-OS (German Published Specification) No. 2,429,523) and N-trichloromethylmercapto-tetrahydrophthalimide (compare K. H. Büchel, Pflanzenschutz and Schädlingsbekämpfung (Plant Protection and Combating Pests), page 140, Georg Thieme Verlag Stuttgart, 1977) have fungicidal properties. However, the activity of these compounds is not always completely satisfactory, especially when relatively low amounts and concentrations are applied.

The present invention now provides, as new compounds, the heterocyclic amide derivatives of the formula $$B-\overset{Y}{\underset{\parallel}{C}}-N\overset{A-X-R^2}{\underset{R^1}{\diagdown}} \quad (I)$$

in which
  $R^1$ represents alkyl, or represents alkenyl which has more than 2 carbon atoms and is optionally substituted by halogen, or represents alkinyl which has more than 2 carbon atoms and is optionally substituted by halogen, or represents alkoxyalkyl or alkylthioalkyl;
  $R^2$ represents optionally substituted naphthyl, or represents optionally substituted tetrahydronaphthyl, or represents optionally substituted indanyl;
  A represents an alkylene bridge, or also an alkenylene bridge if X denotes a direct bond;
  X represents oxygen, sulphur or a direct bond;
  Y represents oxygen or sulphur;
  B represents imidazol-1-yl, pyridin-3-yl, pyrazin-2-yl, pyrimidin-5-yl, 1,2,4-triazol-1-yl or 1-methylimidazol-5-yl;
and acid addition salts and metal salt complexes thereof.

The heterocyclic amide derivatives of the formula (I)

$$B-\overset{Y}{\underset{\parallel}{C}}-N\overset{A-X-R^2}{\underset{R^1}{\diagdown}} \quad (I)$$

in which
  $R^1$, $R^2$, A, X, Y and B have the abovementioned meanings,
are obtained when
  (a) amines of the general formula (II)

$$HN\overset{A-X-R^2}{\underset{R^1}{\diagdown}} \quad (II)$$

in which
  $R^1$, $R^2$, A and X have the abovementioned meanings,
are reacted with carbonyl or thiocarbonyl compounds of the general formula (IIIa)

$$B'-\overset{Y}{\underset{\parallel}{C}}-N\diagup\!\!\!\!\diagdown \quad (IIIa)$$

in which
  Y represents oxygen or sulphur and
  B' represents imidazolyl-1-yl, pyridin-3-yl, pyrazin-2-yl, pyrimidin-5-yl or 1-methylimidazol-5-yl,
or with carbonyl or thiocarbonyl compound of the general formula (IIIb)

$$\overset{N=\diagdown}{\underset{=N}{\diagup}}N-\overset{Y}{\underset{\parallel}{C}}-N\overset{\diagup=N}{\underset{N=}{\diagdown}} \quad (IIIb)$$

in which
  Y represents oxygen or sulphur,
in the presence of a suitable inert organic solvent; or
  (b) amines of the general formula (II)

$$HN\overset{A-X-R^2}{\underset{R^1}{\diagdown}} \quad (II)$$

in which
  $R^1$, $R^2$, A and X have the abovementioned meanings, are reacted with carbamyl chloride compounds of the formula (IV)

$$B''-\overset{O}{\underset{\parallel}{C}}-Cl \quad (IV)$$

in which
  B'' represents pyridin-3-yl, pyrazin-3-yl, pyrazin-2-yl, pyrimidin-5-yl or 1-methylimidazol-5-yl,
in the presence of a suitable inert organic solvent and in the presence of an acid-binding agent; or
  (c) carbamyl chloride or thiocarbamyl chloride derivatives of the general formula (V)

$$Cl-\overset{Y}{\underset{\parallel}{C}}-N\overset{A-X-R^2}{\underset{R^1}{\diagdown}} \quad (V)$$

in which
  $R^1$, $R^2$, A, X and Y have the abovementioned meanings, are reacted with azoles of the general formula (VI)

$$\overset{M}{\underset{N}{\diagdown}}\overset{|}{N}\diagdown_Z \quad (VI)$$

in which
  Z represents a nitrogen atom or the CH group and
  M represents hydrogen or an alkali metal, in the presence of a suitable inert organic solvent and, if appropriate, in the presence of an acid-binding agent; or (d) carboxamide of the formula (Ia)

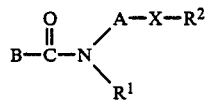

in which

R¹, R², A, X and B have the abovementioned meanings, are reacted with phosphorus pentasulphide in the presence of an inert organic solvent.

If appropriate, an acid or a metal salt can then be added onto the compounds of the formula (I) thus obtained.

The new heterocyclic amide derivatives of the formula (I) and their acid addition salts and metal salt complexes have powerful fungicidal properties. Surprisingly, the compounds according to the invention thereby exhibit a more powerful action than N-[2-(2,4,6-trichlorophenoxy)-ethyl]-N-propyl-1H-imidazole-1-carboxamide and N-trichloromethylmercaptotetrahydrophthalimide, which are known from the prior art and are closely related compounds structurally and from the point of view of their action. The substances according to the invention thus represent an enrichment of the art.

Formula (I) provides a general definition of the heterocyclic amide derivatives according to the invention. Preferably, in this formula, R¹ represents alkyl with 1 to 12 carbon atoms, or represents alkenyl or alkinyl which has in each case 3 to 12 carbon atoms and is optionally monosubstituted or polysubstituted by identical or different substituents from the group comprising fluorine and chlorine, wherein the multiple bond in each case must not be in the α-position relative to the nitrogen atom, or represents alkoxyalkyl or alkylthioalkyl with in each case 1 to 6 carbon atoms in the alkoxy or alkylthio part and 2 to 6 carbon atoms in the alkyl part;

R² represents naphthyl, tetrahydronaphthyl or indanyl, optionally monosubstituted, disubstituted or trisubstituted by identical or different substituents, substituents which may be mentioned in each case being: alkyl with 1 to 4 carbon atoms, halogen and halogenoalkoxy with 1 to 4 carbon atoms and 1 to 5 identical or different halogen atoms, such as, in particular, fluorine and chlorine atoms;

A represents a straight-chain or branched alkylene bridge with 1 to 8 carbon atoms if X denotes a direct bond; or represents a straight-chain or branched alkylene bridge with 2 to 8 carbon atoms if X denotes oxygen or sulphur, but wherein there must be at least 2 carbon atoms between the nitrogen atom and the radical X; or represents a straight-chain or branched alkylene bridge with 3 to 8 carbon atoms, wherein the double bond must not be in the α-position relative to the nitrogen atom;

X represents oxygen, sulphur or a direct bond;

Y represents oxygen; and

B represents imidazol-1-yl, pyridin-3-yl, pyrazin-2-yl, pyrimidin-5-yl, 1,2,4-triazol-1-yl or 1-methylimidazol-5-yl.

Particularly preferred compounds of the formula (I) are those
in which

R¹ represents straight-chain or branched alkyl with 1 to 10 carbon atoms, or represents alkenyl or alkinyl which has in each case 3 to 10 carbon atoms and is optionally monosubstituted, disubstituted or trisubstituted by identical or different substituents from the group comprising fluorine or chlorine, wherein the multiple bond in each case must not be in the α-position relative to the nitrogen atom, or represents alkoxyalkyl or alkylthioalkyl with in each case 1 to 4 carbon atoms in the alkoxy or alkylthio part and 2 to 4 carbon atoms in the alkyl part;

R² represents naphthyl, tetrahydronaphthyl or indanyl, optionally monosubstituted or disubstituted by identical or different substituents, substituents which may be mentioned in each case being fluorine, chlorine bromine and trifluoromethoxy;

A represents a straight-chain or branched alkylene bridge with 1 to 6 carbon atoms if X denotes a direct bond; or represents a straight-chain or branched alkylene bridge with 2 to 6 carbon atoms if X denotes oxygen or sulphur, but wherein there must be at least 2 carbon atoms between the nitrogen atom and the radical X, or represents an alkylene bridge with 3 to 5 carbon atoms, wherein the double bond must not be in the α-position relative to the nitrogen atom;

X represents oxygen, sulphur or a direct bond;

Y represents oxygen; and

B represents imidazol-1-yl, pyrazin-2-yl or pyridin-3-yl.

Especially preferred compounds of the formula (I) are those
in which

R¹ represents straight-chain or branched alkyl with 2 to 8 carbon atoms straight chain or branched alkenyl or alkinyl with, in each case, 3 to 8 carbon atoms, wherein the multiple bond in each case must not be in the α-position relative to the nitrogen atom or represents methoxyethyl, ethoxyethyl, n-propoxyethyl, methylthioethyl, ethylthioethyl or n-propylthioethyl;

R² represents naphthyl, tetrahydronaphthyl or indanyl, optionally monosubstituted or disubstituted by identical or different substituents, substituents which may be mentioned being fluorine, chlorine and trifluoromethoxy;

A represents a straight-chain or branched alkylene bridge with 1 to 4 carbon atoms if X denotes a direct bond; or represents a straight-chain or branched alkylene bridge with 2 to 4 carbon atoms if X denotes oxygen or sulphur, but wherein there must be at least 2 carbon atoms between the nitrogen atom and the radical X, or represents an alkenylene bridge with 3 carbon atoms, wherein the double bond must not be in the α-position relative to the nitrogen atom;

X represents oxygen, sulphur or a direct bond;

Y represents oxygen; and

B represents imidazol-1-yl or pyridin-3-yl.

Addition products of acids and those heterocyclic amide derivatives of the formula (I) in which the substituents R¹, R², A, X, Y and B have the meanings which have already been mentioned as preferred for these substituents are also preferred compounds according to the invention.

The acids which can be added on include, preferably, hydrogen halide acids, such as, for example, hydrochloric acid and hydrobromic acid, in particular hydrochloric acid, and furthermore phoshoric acid, nitric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

Addition products of salts of metals of main group II to IV and sub-group I and II and IV to VIII and those substituted heterocyclic amide derivatives of the formula (I) in which the substituents $R^1$, $R^2$, A, X, Y and B have the meanings which have already been mentioned as preferred for these substituents are also preferred compounds according to the invention.

Salts of copper, zinc, manganese, magnesium, tin, iron and nickel are particularly preferred here. Possible anions of these salts are those which are derived from acids which lead to physiologically acceptable acid products. Particularly preferred acids of this type in this connection are the hydrogen halide acids, such as, for example, hydrochloric acid and hydrobromic acid, and furthermore phosphoric acid, nitric acid and sulphuric acid.

The following compounds of the general formula (I) may be mentioned specifically, in addition to the compounds mentioned in the preparation examples:

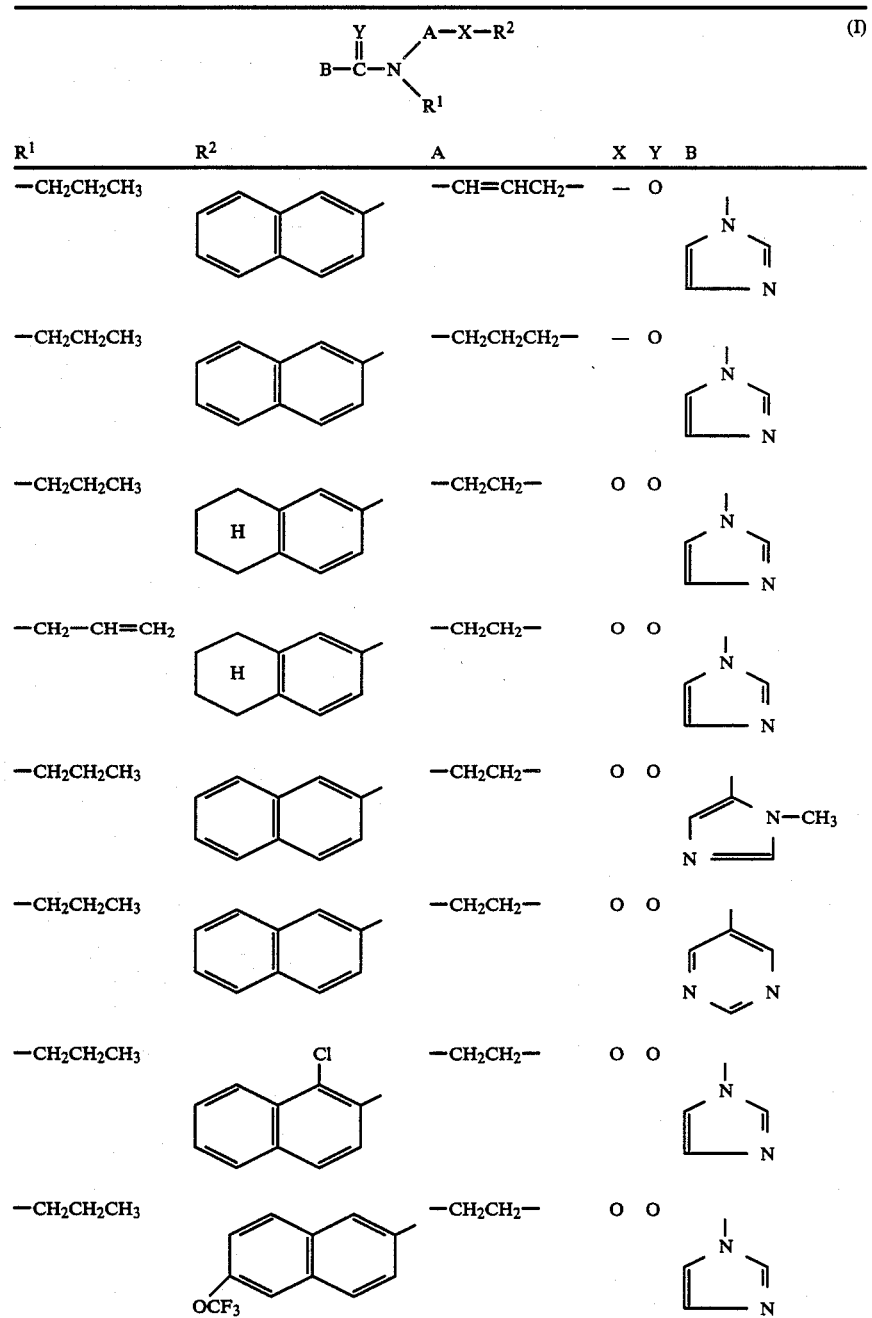

-continued $$\underset{R^1}{\underset{|}{B-\overset{Y}{\underset{\|}{C}}-N}}\diagdown A-X-R^2 \qquad (I)$$

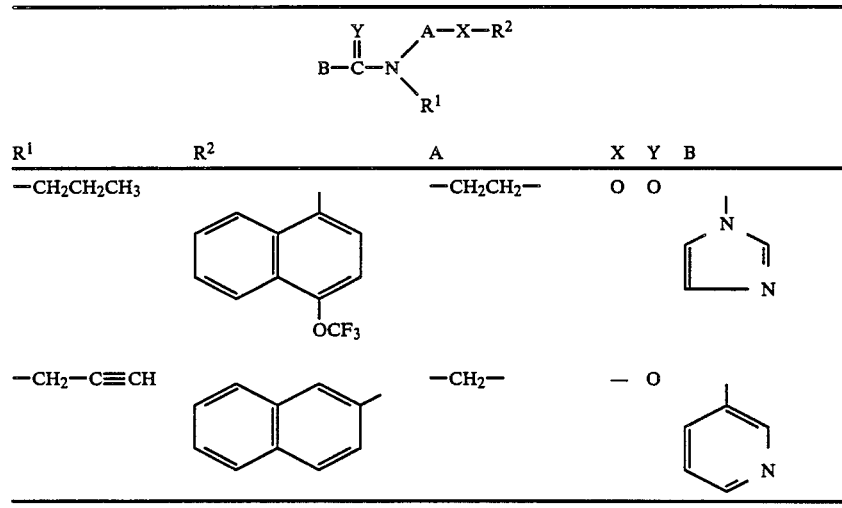

If, for example, N-methyl-N-(2-naphthylmethyl)-amine and N,N'-carbonyldiimidazole ae used as starting substances, the course of process (a) according to the invention can be represented by the following equation:

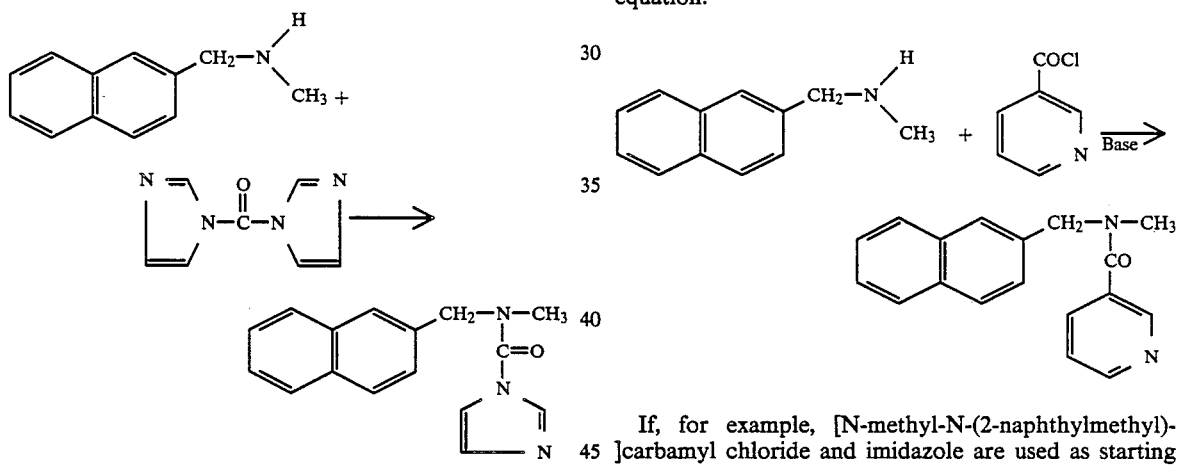

If pyrazine-2-carbon-imidazolide is employed instead of N,N'-carbonyldiimidazole, the equation of the reaction is as follows:

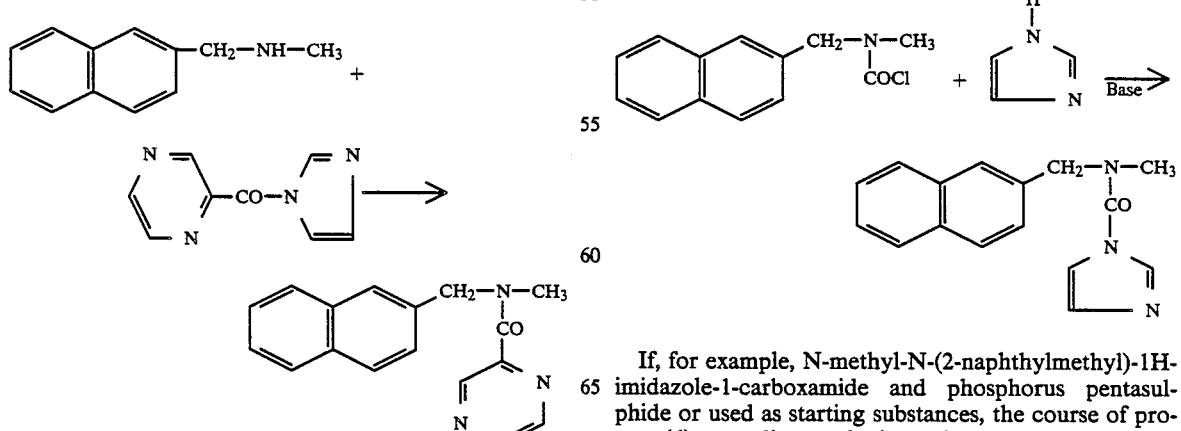

If, for example, N-methyl-N-(2-naphthylmethyl)-amine and pyridin-3-ylcarbamyl chloride are used as starting substances, the course of process (b) according to the invention can be represented by the following equation:

If, for example, [N-methyl-N-(2-naphthylmethyl)-]carbamyl chloride and imidazole are used as starting substances, the course of process (c) according to the invention can be represented by the following equation:

If, for example, N-methyl-N-(2-naphthylmethyl)-1H-imidazole-1-carboxamide and phosphorus pentasulphide or used as starting substances, the course of process (d) according to the invention can be represented by the following equation:

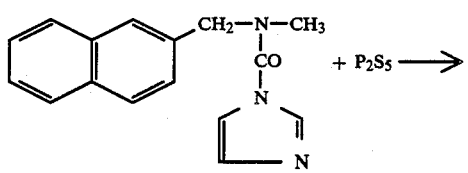

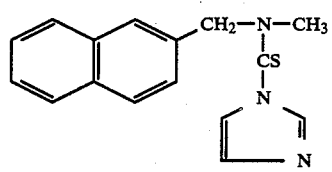

Formula (II) provides a general definition of the amines to be used as starting substances for carrying out process (a) and (b) according to the invention. In this formula, $R^1$, $R^2$, A and X preferably have those meanings which have already been mentioned as preferred for these substituents in connection with the description of the substances of the formula (I) according to the invention.

The amines of the formula (II) are known in some cases (compare, for example, Helv. Chim. Acta 62, 1268 (1979) or Chem. Abstr. 80, 36 897p (1974)) and they can be obtained, for example, by reacting the corresponding amide derivatives with lithium aluminium hydride in the presence of tetrahydrofuran at reflux temperature. The amide derivatives are obtained by adding thionyl chloride to the corresponding carboxylic acid under reflux and adding the corresponding amine to the resulting carbonyl acid chloride in the presence of tetrahydrofuran at room temperature (compare also the preparation examples).

Formulae (IIIa) and (IIIb) provide general definitions of the carbonyl and thiocarbonyl compounds also to be used as starting substances for carrying out process (a) according to the invention. In these formulae, B' and Y preferably have the abovementioned meanings.

The carbonyl and thionylcarbonyl compounds of the formulae (IIIa) and (IIIb) are known (compare, for example, Chem. Ber. 95, 1275 (1962) and Liebigs Annalen der Chemie 609, 75 (1957)). The compounds of the formula (IIIb) can be obtained by reacting triazole with phosgene or thiophosgene in the presence of tetrahydrofuran at room temperature; the compounds of the formula (IIIa) can be obtained by reacting the corresponding carboxylic acid with N,N'-carbonyldiimidazole in the presence of tetrahydrofuran, with gentle warming. The carboxylic acids required for this are generally known. Thus, 5-pyridinecarboxylic acid can be obtained by first reacting 5-bromopyridine with n-butyllithium at −110° C. in the presence of, for example, absolute ether or tetrahydrofuran and then adding solid carbon dioxide (J. Org. Chem. 27, 2264 (1962)). 1-Methyl-5-imidazolecarboxylic acid can be obtained by reacting 1-methyl-4,5-imidazoledicarboxylic acid with acetic anhydride at elevated temperature (compare Bull. Chem. Soc. Japan 53, 557 (1980). 1-Methyl-4,5-imidazoledicarboxylic acid can be obtained by reacting diethyl 4,5-imidazoledicarboxylate with methyl iodide and sodium methylate in the presence of ethanol at the reflux temperature and then hydrolysing the product (compare Journal of Heterocyclic Chemistry 1, 275 (1964)).

Formula (IV) provides a general definition of the carbamyl chloride compounds also to be used as starting substances for carrying out process (b) according to the invention. In this formula, B" preferably has the abovementioned meaning.

The carbamoyl chloride compounds of the formula (IV) are known (compare, for example, Liebigs Annalen der Chemie 766, 73 (1972); Bull. Chem. Soc. Japan 53, 557 (1980); Rec. trav. chim. 80, 1372 (1961)), or the can be obtained by the processes described therein, by adding thionyl chloride to the corresponding carboxylic acids under reflux (compare also the preparation examples).

Formula (V) provides a general definition of the carbamyl chlorides to be used as starting substances for carrying out process (c) according to the invention. In this formula, $R^1$, $R^2$, A, X and Y preferably have the meanings which have already been given as preferred for those substituents in connection with the description of the substances of the formula (I) according to the invention.

The carbamyl chlorides of the formula (V) can be obtained in generally known manner by reacting amines of the formula (III) with phosgene or thiophosgene in the presence of a suitable inert organic solvent, such as, for example, acetonitrile, ethyl acetate, toluene, methylene chloride or dioxane, at temperatures between 20° C. and 140° C.

Formula (VI) provides a general definition of the azoles also to be used as starting substances for carrying out process (c) according to the invention. In this formula, Z represents a nitrogen atom or the CH group. M preferably represents hydrogen, sodium or potassium.

The azoles of the formula (VI) are generally known compounds of organic chemistry.

The heterocyclic amine derivatives of the formula (Ia) to be used as starting substances for carrying out process (d) according to the invention are compounds according to the invention and can be prepared by processes (a), (b) and (c) according to the invention.

Process (a) according to the invention is carried out in the presence of an inert organic solvent. Inert organic solvents include, preferably, nitriles, such as acetonitrile; esters, such as ethyl acetate; ethers, such as dioxane; aromatic hydrocarbons, such as toluene; chlorinated hydrocarbons, such as methylene chloride; acid amides, such as dimethylformamide; and sulphoxide, such as dimethylsulphoxide. Preferably, the solvent is employed in absolute form.

The reaction temperatures can be varied within a substantial range in carrying out process (a) accorrding to the invention. In general, the reaction is carried out at temperatures between 20° C. and 140° C., preferably between 50° C. and 120° C.

The reaction in process (a) according to the invention can be carried out under normal pressure, but also under increased pressure. The reaction is in general carried out under pressures between 1 and 50 bar, preferably between 1 and 25 bar.

Process (b) according to the invention is carried out in the presence of an inert organic solvent. Inert organic solvents include, preferably, nitriles, such as acetonitrile; esters, such as ethyl acetate; ethers, such as dioxane; aromatic hydrocarbons, such as toluene and chlorinated hydrocarbons, such as methylene chloride.

Possible acid-binding agents for process (b) according to the invention are all the bases which can usually be employed. These include, preferably, teriary amines, such as triethylamine or pyridine; alkali metal hydroxides and alkali metal carbonates.

The reaction temperatures can be varied within a substantial range in carrying out process (b) according to the invention. The reaction is in general carried out at temperatures between 0° C. and 120° C., preferably at temperatures between 10° C. and 100° C.

Process (c) according to the invention is carried out in the presence of an inert organic solvent. Inert organic solvents include, preferably, nitriles, such as acetonitrile; esters, such as ethyl acetate; ethers, such as dioxane; aromatic hydrocarbons, such as toluene, and chlorinated hydrocarbons, such as methylene chloride.

Possible acid-binding agents for process (c) according to the invention are all the bases which can usually be employed. These include, preferably, tertiary amines, such as triethylamine or pyridine, and an excess of imidazole or triazole.

The reaction temperatures can be varied within a substantial range in carrying out process (c) according to the invention. The reaction is in general carried out at temperatures between 20° C. and 150° C., preferably at temperatures between 50° C. and 120° C.

The reaction in process (c) according to the invention can be carried out under normal pressure, but also under increased pressure. The raction is in general carried out under pressures between 1 and 50 bar, preferably between 1 and 25 bar.

Process (c) according to the invention is carried out in the presence of an inert absolute organic solvent. Inert absolute organic solvents include, preferably, nitriles, such as acetonitrile; ethers, such as dioxane; aromatic hydrocarbons, such as toluene, and chlorinated hydrocarbons, such as methylene chloride.

The reaction temperatures can be varied within a substantial range in carrying out process (d) according to the invention. The reaction is in general carried out at temperatures between 0° C. and 80° C., preferably at temperatures between 10° C. and 60° C.

Process (d) according to the invention is preferably carried out in an ultrasonic bath so that the dispersion of the phosphorus pentasulphide in the solvent is facilitated.

Those acids which have already been mentioned as preferred acids in connection with the description of the acid addition salts according to the invention are preferably suitable for the preparation of acid addition salts of the compounds of the general formula (I).

The acid addition salts of the compounds of the formula (I) can be obtained in a simple manner by customary salt formation methods, for example by dissolving a compound of the general formula (I) in a suitable inert solvent and adding the acid, for example hydrochloric acid, and they can be isolated in a known manner, for example by filtration, and if appropriate purified by washing with an inert organic solvent.

Those salts of metals which have already been described above are preferably suitable for the preparation of metal salt complexes of the compounds of the general formula (I).

The metal salt complexes of compounds of the general formula (I) can be obtained in a simple manner by customary processes, thus, for example, by dissolving the metal salt in alcohol, for example ethanol, and adding the solution to compounds of the general formula (I). Metal salt complexes can be purified in a known manner, for example by filtration, isolation and, if appropriate, by recrystallisation.

The active compounds according to the invention exhibit a powerful micrbiocidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Xanthomonas species, such as, for example, *Xanthomonas campestris* pv. oryzae; Pseudomonas species, such as, for example, *Pseudomonas syringae* pv. Lachrymans; Erwinia species, such as, for example, *Erwinia amylovora;* Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubense;* Plasmopara species, such as, for example, *Plasmopara viticola;* Peronospora species, such as, for example, *Peronospora pisi* or *P. brassica;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea;* (conidia form: Drechslera, syn: Helminthosporium); Cochliobolus species, such as, for example, *Cochliobolus sativus;* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Venturia species, such as *Venturia inaequalis* on apple, and Puccinia species, such as *Puccinia recondita* on wheat, and also for combating powdery mildew, *Botrytis cinerea, Cochliobolus sativus, Pyrenophora teres* and Fusarium on cereals and Pyricularia on rice. The good in vitro action against *Pyricularia oryzae* on rice is to be emphasised.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylene or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of the active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellants, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomising, misting, vaporising, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The present invention also provides a fungicidal composition containing as active ingredient a compound of the formula (I) according to the present invention in admixture with a solid diluent or carrier containing a surface-active agent.

The present invention also provides a method of combating fungi which comprises applying to the fungi, or to a habitat thereof, a compound of the formula (I) according to the present invention alone or in the form of a composition containing as active ingredient a compound of the formula (I) according to the present invention in admixture with a diluent or carrier.

The preparation and use of the substances according to the invention can be seen from the examples which follow.

PREPARATION EXAMPLES

EXAMPLE 1

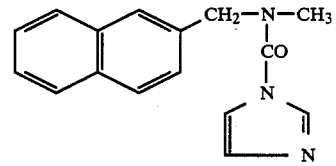

(Process a)

A solution of 20 g (0.12 mole) of N-methyl-N-(2-naphthylmethyl)-amine and 21.1 g (0.13 mole) of N,N'-carbonyldiimidazole in 150 ml of absolute acetonitrile is heated under reflux for 4 hours. After removal of the solvent, the residue is taken up in ethyl acetate and the mixture is washed three times with water, dried and concentrated.

30.9 g (that is to say 97% of theory) of [N-methyl-N-(2-naphthylmethyl)]-1H-imidazole-1-carboxamide of melting point 94.5°–95.5° C. are obtained.

Preparation of the starting substances

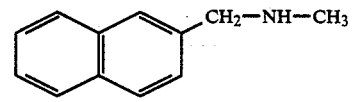

A solution of 105.2 g (0.57 mole) of [N-methyl]naphthalene-2-carboxamide in 450 ml of absolute tetrahydrofuran is added dropwise to a suspension of 26.5 g (0.7 mole) of lithium aluminium hydride in 450 ml of absolute ether and the mixture is then heated under reflux for 3 hours.

After working up, 96 g (98% of theory) of N-methyl-N-(2-naphthyl)-methylamine are obtained as a light brown oil of 98% purity.

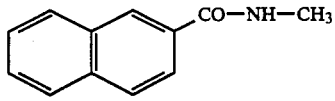

A solution of 100 g (0.58 mole) of naphthalene-2-carboxylic acid in 220 ml of thionyl chloride is heated under reflux for 1 hour and the excess thionyl chloride is then distilled off. The residue is suspended in 750 ml of tetrahydrofuran and 91 g (0.9 mole) of 30% strength aqueous methylamine solution are added, while cooling and stirring. 200 ml of triethylamine are then rapidly added dropwise. The mixture is stirred overnight at room temperature. After removal of the solvent, the residue is partitioned between methylene chloride and water.

105.2 g (98% of theory) of [N-methyl]-naphthalene-2-carboxamide of melting point 108°–109° C. are obtained.

EXAMPLE 2

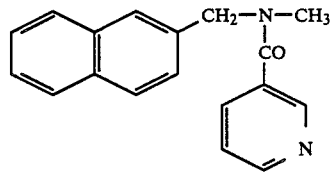

(Process b)

A solution of 31 g (0.25 mole) of 3-pyridinecarboxylic acid in 120 ml of thionyl chloride is heated under reflux for 1 hour and the excess thionyl chloride is then distilled off in vacuo. The residue is suspended in 400 ml of absolute tetrahydrofuran, and 30 g (0.18 mole) of N-methyl-N-(2-naphthyl)-methylamine are added dropwise at room temperature, with stirring, 64.3 g (0.625 mole) of triethylamine are then added dropwise and the reaction mixture is stirred at room temperature overnight. The tetrahydrofuran is removed, the residue is partitioned between methylene chloride and water and the methylene chloride phase is separated off, washed once with a saturated sodium bicarbonate solution and then twice with water, dried and concentrated.

42.7 g (86% of theory) of [N-methyl-N-(2-naphthyl)-methyl]-3-pyridinecarboxamide are obtained as a viscous oil. NMR δ (CDCl$_3$) 8.9–8.5 and 7.9–7.0 (11H); 4.87 and 4.65 (2H, 2s, broad); 3.07 and 2.90 (3H, 2s, broad).

The following compounds of the general formula (I)

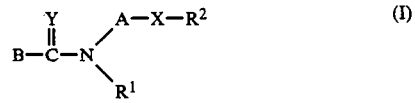

are obtained in an analogous manner and by the processes according to the invention:

| Serial No. | R¹ | R² | A | X | Y | B | Melting point (°C.) or spectroscopic data |
|---|---|---|---|---|---|---|---|
| 3 | —CH₂CH₂CH₃ | naphthyl | —CH₂CH₂— | O | O | imidazole | 54–56 |
| 4 | —CH₃ | naphthyl | —CH₂CH₂— | O | O | imidazole | 96.5 |
| 5 | —CH₂CH₃ | naphthyl | —CH₂CH₂— | O | O | imidazole | 87–88 |
| 6 | —CH₂CH=CH₂ | naphthyl | —CH₂CH₂— | O | O | imidazole | 80 |
| 7 | —CH₂CH₂CH₃ | naphthyl | —CH₂CH₂— | O | O | imidazole | resin/¹H—NMR CDCl₃: 3.46(2H, t) for N—CH₂—CH₂CH₂CH₃; 3.80(2H, t) for OCH₂—CH₂—N |
| 8 | —CH₂CH₂CH₃ | naphthyl | —CH₂— | — | O | imidazole | resin/¹H—NMR CDCl₃: δ 4.78(2H, s) for Naphthyl—CH₂—N; δ 3.36(2H, t) for N—CH₂—CH₂—N |
| 9 | —CH₂CH₂CH₃ | naphthyl | —CH₂CH₂— | O | O | pyridyl | resin/¹H—NMR CDCl₃: 3.20–3.65(2H, 's' broad) for N—CH₂—CH₂CH₃; 3.58–4.12(2H, 's', broad) for OCH₂—CH₂—N |

-continued

| Serial No. | R¹ | R² | A | X | Y | B | Melting point (°C.) or spectroscopic data |
|---|---|---|---|---|---|---|---|
| 10 | —CH₂CH₂CH₃ | naphthyl | —CH₂CH₂— | O | O | pyrimidinyl | |
| 11 | —CH₂CH₂CH₃ | naphthyl | —CH₂CH₂— | O | O | imidazolyl | 63.5 |
| 12 | —CH₂CH₂CH₃ | naphthyl | —CH₂CH₂— | O | O | pyridyl | oil |
| 13 | —CH₂CH₂CH₃ | naphthyl | —CH₂CH₂— | — | O | imidazolyl | ¹H—NMR CDCl₃ δ 3.27(2H, t, z=5Hz) for N—CH₂—CH₂—CH₃ δ 3.05(2H, t, z=5Hz) for naphthyl—CH₂—CH₂—N |
| 14 | —CH₂CH₂CH₃ | naphthyl | —CH₂CH₂— | — | O | imidazolyl | |
| 15 | —CH₂CH₂OCH₃ | naphthyl | —CH₂CH₂— | O | O | imidazolyl | 56-57 |
| 16 | —CH₂CH₂CH₃ | naphthyl | —CH₂CH₂— | S | O | imidazolyl | |

-continued

| Serial No. | R¹ | R² | A | X | Y | B | Melting point (°C.) or spectroscopic data |
|---|---|---|---|---|---|---|---|
| 17 | —CH₂CH₂CH₃ | naphthyl | —CH₂CH₂— | O | O | pyrazole | |
| 18 | —CH₂CH₃ | naphthyl | —CH₂— | — | O | imidazole | Oil/¹H—NMR CDCl₃: δ 4.08(2H, s) for Naphthyl—CH₂—N=; δ 3.48(2H, q) for N—CH₂—CH₃ |
| 19 | —CH₂CH₂CH₂CH₃ | naphthyl | —CH₂— | — | O | imidazole | Oil/¹H—NMR CDCl₃: δ 4.78(2H, s) for Naphthyl—CH₂—N; δ 3.39(2H, t) for N—CH₂—CH₂ |
| 20 | —CH₂CH=CH₂ | naphthyl | —CH₂— | — | O | imidazole | Resin/¹H—NMR CDCl₃: δ 4.77(2H, s) for Naphthyl—CH₂—N; δ 3.96(2H, d) for N—CH₂—CH= |
| 21 | —CH₂CH₃ | naphthyl | —CH₂— | — | O | pyridyl | Resin/¹H—NMR CDCl₃: δ 5.08–4.50(2H, s, broad) for Naphthyl—CH₂—N; δ 3.85–2.90(2H, s) for N—CH₂—CH₃ |
| 22 | —CH₂CH₂CH₃ | naphthyl | —CH₂— | — | O | pyridyl | Resin/¹H—NMR CDCl₃: δ 5.08–4.50, (2H, d, broad) for Naphthyl—CH₂—N; δ 3.70–2.97(2H, d, broad) for N—CH₂—CH₂ |
| 23 | —CH₂CH₂CH₂CH₃ | naphthyl | —CH₂— | — | O | pyridyl | Resin/¹H—NMR CDCl₃: δ 5.08–4.50(2H, d, broad) for Naphthyl—CH₂—N; δ 3.75–2.95(2H, d, broad) for N—CH₂—CH₂ |

-continued

| Serial No. | R¹ | R² | A | X | Y | B | Melting point (°C.) or spectroscopic data |
|---|---|---|---|---|---|---|---|
| 24 | —CH₂CH=CH₂ | 2-naphthyl | —CH₂— | — | O | pyridyl | Resin/¹H—NMR CDCl₃: δ 5.08–4.50(2H, s, broad) for Naphthyl—CH₂—N; δ 4.30–3.60(2H, d, broad) for N—CH₂—CH= |
| 25 | —CH₂CH₂CH₃ | | —CH₂CH₂— | O | O | pyridyl | Resin/¹H—NMR CDCl₃: δ 3.18–3.65(2H,'s', broad) for N—CH₂—CH₂CH₂CH₃; δ 3.60–4.12(2H,'s', broad) for OCH₂—CH₂—N |
| 26 | —CH₃ | | —CH₂CH₂— | O | O | pyridyl | Resin/¹H—NMR CDCl₃: δ 3.20(3H, s) for N—CH₃; δ 3.70–4.18(2H,'s', broad) for CH₂—N |
| 27 | —CH₂CH₃ | | —CH₂CH₂— | O | O | pyridyl | Resin/¹H—NMR CDCl₃: δ 3.28–3.82(2H,'s', broad) for N—CH₂—CH₃; δ 3.65–4.12(2H,'s', broad) for CH₂—N |
| 28 | —CH₂—CH=CH₂ | 2-naphthyl | —CH₂—CH₂— | O | O | pyridyl | oil |
| 29 | —CH₃ | 1-naphthyl | —CH₂—CH₂— | O | O | imidazolyl | 81.5–82.5 |
| 30 | —CH₃ | 1-naphthyl | —CH₂—CH₂— | O | O | pyridyl | oil |

-continued

| Serial No. | R¹ | R² | A | X | Y | B | Melting point (°C.) or spectroscopic data |
|---|---|---|---|---|---|---|---|
| 31 | —CH₂—CH₃ | naphthyl | —CH₂—CH₂— | O | O | imidazolyl | 92.5 |
| 32 | —CH₂—CH₃ | naphthyl | —CH₂—CH₂— | O | O | pyridyl | oil |
| 33 | —(CH₂)₃—CH₃ | naphthyl | —CH₂—CH₂— | O | O | imidazolyl | 87.5 |
| 34 | —(CH₂)₃—CH₃ | naphthyl | —CH₂—CH₂— | O | O | pyridyl | oil |
| 35 | —CH₂—CH=CH₂ | naphthyl | —CH₂—CH₂— | O | O | imidazolyl | 80–81 |
| 36 | —(CH₂)₃—CH₃ | naphthyl | —CH₂—CH₂ | — | O | imidazolyl | ¹H—NMR CDCl₃: δ 3.30(2H, t, τ=5Hz) for N—CH₂—CH₂—CH₂—CH₃, δ 3.05(2H, t, τ=5Hz), for Naphthyl—CH₂—N |
| 37 | —(CH₂)₃—CH₃ | naphthyl | —CH₂—CH₂ | — | O | phenyl | ¹H—NMR CDCl₃: δ 3.96–3.38(3H, 'S', breit) and 3.38–2.78(3H, 'S', broad), for Naphthyl—CH₂—CH₂—N—CH₂—CH₂—CH₂—CH₃ |

-continued

| Serial No. | R¹ | R² | A | X | Y | B | Melting point (°C.) or spectroscopic data |
|---|---|---|---|---|---|---|---|
| 38 | —(CH₂)₂—CH₃ | naphthyl | —CH₂—CH₂— | — | O | pyridyl | ¹H—NMR CDCl₃: δ 3,94–3,36(3H, 'S', broad) and 3,36–2,73(3H, 'S', broad), for Naphthyl—CH₂—CH₂—N—CH₂—CH₂—CH₃ |
| 39 | —CH₂—CH=CH₂ | naphthyl | —CH₂—CH₂— | O | O | pyridyl | ¹H—NMR CDCl₃: δ 4,27–3,88(4H, 'S', broad), for Naphthyl—O—CH₂—CH₂—N—CH₂—CH=CH₂ |
| 40 | —CH₂—CH₃ | naphthyl | —CH₂—CH₂— | — | O | imidazolyl | ¹H—NMR CDCl₃ (300 MHz): δ 3,44(2H, t) for Naphthyl—CH₂—CH₂—N—C₂H₅; δ 3,37(2H, q), fur N—CH₂—CH₃ |
| 41 | —(CH₂)₃—CH₃ | naphthyl | —CH₂—CH₂— | — | O | imidazolyl | ¹H—NMR CDCl₃ (300 MHz): δ 3,41(2H, t) for Naphthyl CH₂—CH₂—N—C₄H₉ δ 3,26(2H,t), for —N—CH₂—C₃H₇ |
| 42 | —(CH₂)₄—CH₃ | naphthyl | —CH₂—CH₂— | O | O | imidazolyl | |
| 43 | —(CH₂)₅—CH₃ | naphthyl | —CH₂—CH₂— | O | O | imidazolyl | |
| 44 | —(CH₂)₆—CH₃ | naphthyl | —CH₂—CH₂— | O | O | imidazolyl | |

-continued

| Serial No. | R¹ | R² | A | X | Y | B | Melting point (°C.) or spectroscopic data |
|---|---|---|---|---|---|---|---|
| 45 | —(CH₂)₄—CH₃ | naphthyl | —CH₂— | — | O | imidazole | |
| 46 | —(CH₂)₅—CH₃ | naphthyl | —CH₂— | — | O | imidazole | |
| 47 | —(CH₂)₆—CH₃ | naphthyl | —CH₂— | — | O | imidazole | |
| 48 | —(CH₂)₂—CH₃ | 6-Br-naphthyl | —CH₂—CH₂— | O | O | imidazole | 112–114 |

Use Examples

The substances shown below are employed as comparison compounds in the use examples which follow:

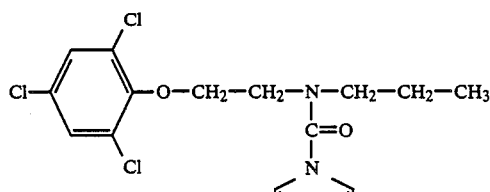

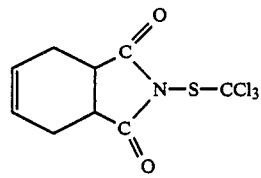

Example A

Puccinia test (wheat)/protective/
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of *Puccinia recondita* with a 0.1% strength aqueous agar solution. After the spore suspension has dried on, the plants are sprayed with the preparation of active compound until dew-moist. The plants remain in an incubation cabin at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, a clearly superior activity compared with the prior art is shown, for example, by the compound according to the preparation example 3.

Example B

Venturia test (apple)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compound according to the preparation example 3.

It will be understood that the specification and examples are illustrative, but not limitative of the present invention and that other embodiments within the spirit and scope of the invention will suggest themselves to those skilled in the art.

What is claimed is:

1. A heterocyclic amide derivative of the formula

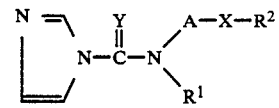

in which

R$^1$ is alkyl with 1 to 12 carbon atoms, alkenyl with 3 to 12 carbon atoms, halogeno-substituted alkenyl with 3 to 12 carbon atoms, alkinyl with 3 to 12 carbon atoms, halogeno-substituted alkinyl with 3 to 12 carbon atoms, alkoxyalkyl with 1 to 6 carbon atoms in the alkoxy part and 2 to 6 carbon atoms in the alkyl part or alkylthioalkyl with 1 to 6 carbon atoms in the alkyl part;

R$^2$ is naphthyl, naphthyl substituted by a substituent selected from the group consisting of alkyl with 1 to 4 carbon atoms, halogen and halogenoalkoxy with 1 to 4 carbon atoms and 1 to 5 identical or different halogen atoms, tetrahydronaphthyl, tetrahydrononaphthyl substituted by a substituent selected from the group consisting of alkyl with 1 to 4 carbon atoms, halogen and halogenoalkoxy with 1 to 4 carbon atoms and 1 to 5 identical or different halogen atoms, indanyl or indanyl substituted by a substituent selected from the group consisting of alkyl with 1 to 4 carbon atoms, halogen and halogenoalkoxy with 1 to 4 carbon atoms and 1 to 5 identical or different halogen atoms;

A is an alkylene bridge with 1 to 8 carbon atoms or, if X denotes a direct bond, is also an alkenylene bridge with 1 to 8 carbon atoms;

X is oxygen, sulphur or a direct bond; and

Y is oxygen or sulphur;

or an acid addition salt or a metal salt complex thereof.

2. Compound as claimed in claim 1, in which

R$^1$ is alkyl with 1 to 12 carbon atoms; alkenyl or alkinyl with, in each case, 3 to 12 carbon atoms, wherein the multiple bond in each case must not be in the α-position relative to the nitrogen atom; substituted alkenyl or substituted alkinyl with in each case 3 to 12 carbon atoms, wherein the multiple bond in each case must not be in the α-position relative to the nitrogen atom, the substituents being selected from the group consisting of fluorine and chlorine; or is alkoxyalkyl or alkylthioalkyl with in each case 1 to 6 carbon atoms in the alkoxy or alkylthio part and 2 to 6 carbon atoms in the alkyl part;

R$^2$ is naphthyl, substituted naphthyl the substituents being selected from the group consisting of alkyl with 1 to 4 carbon atoms, halogen and halogenoalkoxy with 1 to 4 carbon atoms and 1 to 5 identical or different halogen atoms, or is tetrahydronaphthyl, substituted tetrahydronaphthyl the substituents being selected from the group consisting of alkyl with 1 to 4 carbon atoms, halogen and halogenoalkoxy with 1 to 4 carbon atoms and 1 to 5 identical or different halogen atoms, or is indanyl or substituted indanyl the substituents being selected from the group consisting of alkyl with 1 to 4 carbon atoms, halogen and halogenoalkoxy with 1 to 4 carbon atoms and 1 to 5 identical or different halogen atoms;

A is a straight-chain or branched alkylene bridge with 1 to 8 carbon atoms if X denotes a direct bond; or is a straight-chain or branched alkylene bridge with 2 to 8 carbon atoms if X denotes oxygen or sulphur, but wherein there must be at least 2 carbon atoms between the nitrogen atom and the radical X; or is a straight-chain or branched alkylene bridge with 3 to 8 carbon atoms, wherein the double bond must not be in the α-position relative to the nitrogen atom;

X is oxygen, sulphur or a direct bond; and

Y is oxygen;

or an acid addition salt or a metal salt complex thereof.

3. A compound as claimed in claim 1, in which $R^1$ is alkyl with 1 to 10 carbon atoms; alkenyl or alkinyl with, in each case, 3 to 10 carbon atoms, wherein the multiple bond in each case must not be in the α-position relative to the nitrogen atom; mono-, di- or tri-substituted alkenyl or mono-, di- or tri-substituted alkinyl with in each case 3 to 10 carbon atoms, wherein the multiple bond in each case must not be in the α-position relative to the nitrogen atom, the substituents being identical or different and being selected from the group consisting of fluorine and chlorine; or is alkoxyalkyl or alkylthioalkyl with in each case 1 to 4 carbon atoms in the alkoxy or alkylthio part and 2 to 4 carbon atoms in the alkyl part;

$R^2$ is naphthyl or mono-, di- or tri-substituted naphthyl the substituents being identical or different and being selected from the group consisting of fluorine, chlorine, bromine and trifluoromethoxy; or is tetrahydronaphthyl or mono-, di- or tri-substituted tetrahydronaphthyl the substituents being identical or different and being selected from the group consisting of fluorine, chlorine, bromine and trifluoromethoxy; or is indanyl or mono-, di- or tri-substituted indanyl the substituents being identical or different and being selected from the group consisting of fluorine, chlorine, bromine and trifluoromethoxy;

A is a straight-chain or branched alkylene bridge with 1 to 6 carbon atoms if X denotes a direct bond; or is a straight-chain or branched alkylene bridge with 2 to 6 carbon atoms if X denotes oxygen or sulphur, but wherein there must be at least 2 carbon atoms between the nitrogen atom and the radical X, or is an alkylene bridge with 3 to 5 carbon atoms, wherein the double bond must be in the α-position relative to the nitrogen atom;

X, is oxygen, sulphur or a direct bond; and

Y is oxygen;

B is imidazol-1-yl, pyrazin-2-yl or pyridin-3-yl.

4. A compound as claimed in claim 1 in which $R^1$ is straight-chain or branched alkyl with 2 to 8 carbon atoms, straight-chain or branched alkenyl or alkinyl with, in each case, 3 to 8 carbon atoms, wherein the multiple bond in each case must not be in the α-position relative to the nitrogen atom or is methoxyethyl, ethoxyethyl, n-propoxyethyl, methylthioethyl, ethylthioethyl or n-propylthioethyl;

$R^2$ is naphthyl or mono- or di-substituted naphthyl the substituents being identical or different and being selected from the group consisting of fluorine, chlorine and trifluoromethoxy; or is tetrahydronaphthyl or mono- or di-substituted tetrahydronaphthyl the substituents being identical or different and being selected from the group consisting of fluorine, chlorine and trifluoromethoxy; or is indanyl or mono- or di-substituted indanyl the substituents being identical or different and being selected from the group consisting of fluorine, chlorine and trifluoromethoxy;

A is straight-chain or branched alkylene bridge with 1 to 4 carbon atoms if X denotes a direct bond; or is a straight-chain or branched alkylene bridge with 2 to 4 carbon atoms if X denotes oxygen or sulphur, but wherein there must be at least 2 carbon atoms between the nitrogen atom and the radical X, or is an alkenylene bridge with 3 carbon atoms, wherein the double bond must not be in the α-position relative to the nitrogen atom;

X is oxygen, sulphur or a direct bond; and

Y is oxygen;

or an acid addition salt or a metal salt complex thereof.

5. A compound as claimed in claim 1, wherein such compound is [N-methyl-N-(2-naphthylmethyl)]-1H-imidazole-1-carboxamide of the formula

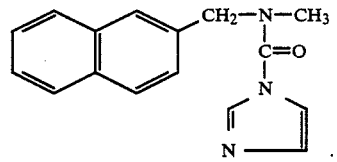

6. A compound as claimed in claim 1, wherein such compound is [N-(n-propyl)-N-(2-naphthyloxy-2-ethyl)]-1H-imidazole-1-carboxamide of the formula

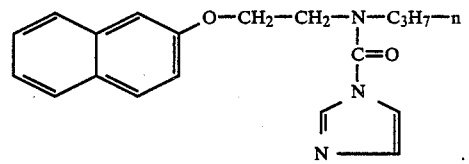

7. A compound as claimed in claim 1, wherein such compound is [N-methyl-N-(2-naphthyloxy-2-ethyl)]-1H-imidazole-1-carboxamide of the formula

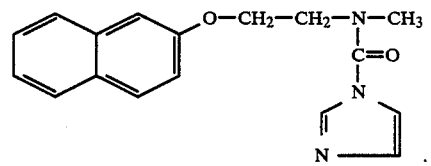

8. A compound as claimed in claim 1, wherein such compound is [N-ethyl-N-(2-naphthyloxy-2-ethyl)]-1H-imidazole-1-carboxamide of the formula

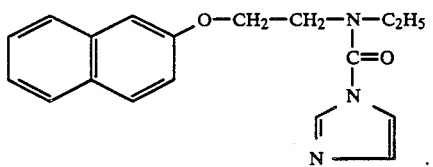

9. A fungicidal composition comprising a fungicidally effective amount of a compound or addition product according to claim 1 in admixture with a diluent.

10. A method of combating fungi which comprises administering to such fungi or to a fungus habitat a fungicidally effective amount of a compound or addition product according to claim 1.

11. The method according to claim 10, wherein such compound is [N-methyl-N-(2-naphthylmethyl)]-1H-imidazole-1-carboxamide,

[N-(n-propyl)-N-(2-naphthyloxy-2-ethyl)]-1H-imidazole-1-carboxamide,

[N-methyl-N-(2-naphthyloxy-2-ethyl)]-1H-imidazole-1-carboxamide or

[N-ethyl-N-(2-naphthyloxy-2-ethyl)]-1H-imidazole-1-carboxamide, or an acid addition salt or a metal salt complex thereof.

12. A heterocyclic amide derivative according to claim 1, wherein $R^1$ is alkyl with 1 to 12 carbon atoms, alkenyl with 3 to 12 carbon atoms, wherein the multiple bond must not be in the α-position relative to the nitrogen atom; or is alkoxyalkyl with 1 to 6 carbon atoms in the alkoxy part and 2 to 6 carbon atoms in the alkyl part;

$R^2$ is naphthyl or halogen substituted naphthyl;

A is a straight-chain or branched alkylene bridge with 1 to 8 carbon atoms if X denotes a direct bond; or is a straight-chain or branched alkylene bridge with 2 to 8 carbon atoms if X denotes oxygen or sulphur, but wherein there must be at least 2 carbon atoms between the nitrogen atom and the radical X;

X is oxygen, sulphur or a direct bond; and

Y is oxygen.

* * * * *

UNITED STATES PATENT AND TRADEMARK OFFICE
CERTIFICATE OF CORRECTION

PATENT NO. : 4,840,961

DATED : June 20, 1989

INVENTOR(S) : Holmwood et al.

It is certified that error appears in the above-identified patent and that said Letters Patent is hereby corrected as shown below:

| | |
|---|---|
| Col. 2, line 42 | After " pyridin-3-yl, " delete " pyrazin-3-yl, " |
| Col. 6, line 7 | After " acceptable " add -- addition -- delete "acid". |
| Col. 8, line 66 | Delete " or " and substitute -- are -- |
| Col. 9, line 31 | Delete " temperature " and substitute -- temperatures -- |
| Col. 10, line 6 | Delete " carbamoyl " and substitute -- carbamyl -- |
| Col. 10, line 10 | Delete " the " and substitute -- they -- |
| Col. 10, line 19 | Delete " those " and substitute -- these -- |
| Col. 10, line 24 | Delete " (III) " and substitute -- (II) -- |
| Col. 10, line 36 | Delete " amine " and substitute -- amide -- |
| Col. 10, line 47 | Delete " sulphoxide " and substitute -- sulphoxides -- |
| Col. 12, line 2 | Delete " micrbiocidal " and substitute -- microbiocidal -- |
| Col. 12, line 23 | Delete " brassica " and substitute -- brassicae -- |
| Col. 13, line 15 | Delete " chloroethylene " and substitute -- chloroethylenes -- |
| Col. 16, line 19 | After " stirring " delete " . " and substitute -- . -- |
| Col. 26, Serial # 36 | Under Melting Point ... delete " 3,30 " and " 3,05 " and substitute -- 3.30 -- and -- 3.05 -- |
| Col. 26, Serial # 37 | Under Melting Point ... delete " 3,96-3,38 " and 3,38-2,78 " and substitute -- 3.96-3.38 -- and -- 3.38-2.78 -- |
| Col. 27, Serial # 38 | Under Melting Point ... delete " 3,94-3,36 " and " 3,36-2,73 " and substitute -- 3.94-3.36 -- and --3.36-2.73 -- |
| Col. 27, Serial # 39 | Under Melting Point ... delete " 4,27-3,88 " and substitute -- 4.27-3.88 -- |
| Col. 27, Serial # 40 | Under Melting Point ... delete " 3,44 " and " 3,37 " and substitute -- 3.44 -- and -- 3.37 -- |
| Col. 27, Serial # 41 | Under Melting Point ... delete " 3,41 " and " 3,26 " and substitute -- 3.41 -- and 3.26-- |

UNITED STATES PATENT AND TRADEMARK OFFICE
CERTIFICATE OF CORRECTION

PATENT NO. : 4,840,961

DATED : June 20, 1989

INVENTOR(S) : Holmwood et al.

It is certified that error appears in the above-identified patent and that said Letters Patent is hereby corrected as shown below:

Col. 33 Claim 3, lines 39-40 last two lines

After " oxygen " delete " ; " and substitute -- , -- also delete " B is imidazol-1-yl, pyrazin-2yl or pyridin-3-yl. " and substitute -- or an acid addition salt or a metal salt complex thereof. --

Col. 34, claim 4, line 28

After " oxygen " delete " ; " and substitute -- , --

Signed and Sealed this

Ninth Day of July, 1991

Attest:

HARRY F. MANBECK, JR.

Attesting Officer

Commissioner of Patents and Trademarks